(12) United States Patent
Li et al.

(10) Patent No.: US 9,814,269 B2
(45) Date of Patent: Nov. 14, 2017

(54) ATOMIZING DEVICE AND ELECTRONIC CIGARETTE HAVING SAME

(71) Applicant: Shenzhen First Union Technology Co., Ltd., Shenzhen, Guangdong Province (CN)

(72) Inventors: Yonghai Li, Shenzhen (CN); Zhongli Xu, Shenzhen (CN); Shuyun Hu, Shenzhen (CN)

(73) Assignee: SHENZHEN FIRST UNION TECHNOLOGY CO., LTD., Shenzhen, Guangdong Province (CN)

( * ) Notice: Subject to any disclaimer, the term of this patent is extended or adjusted under 35 U.S.C. 154(b) by 207 days.

(21) Appl. No.: 14/941,589

(22) Filed: Nov. 14, 2015

(65) Prior Publication Data
US 2016/0135505 A1     May 19, 2016

(30) Foreign Application Priority Data
Nov. 14, 2014  (CN) .................... 2014 2 0680673 U (51) Int. Cl.
| | | |
|---|---|---|
| A24F 13/00 | (2006.01) | |
| A24F 47/00 | (2006.01) | |
| H05B 3/44 | (2006.01) | |
| H05B 3/46 | (2006.01) | |

(52) U.S. Cl.
CPC ............ *A24F 47/008* (2013.01); *H05B 3/44* (2013.01); *H05B 3/46* (2013.01)

(58) Field of Classification Search
CPC ....... A24F 47/008; A24F 47/002; H05B 3/44; H05B 3/46
USPC .................................................. 131/329, 330
See application file for complete search history.

(56) References Cited

U.S. PATENT DOCUMENTS

| | | | |
|---|---|---|---|
| 9,427,536 B2 * | 8/2016 | Fang ..................... | A24F 47/008 |
| 9,603,387 B2 * | 3/2017 | Liu ........................ | A24F 47/008 |
| 9,603,389 B2 * | 3/2017 | Chen ..................... | A24F 47/008 |
| 9,661,878 B2 * | 5/2017 | Liu ........................ | A24F 47/008 |
| 9,675,116 B2 * | 6/2017 | Liu ........................ | A24F 47/008 |

\* cited by examiner

*Primary Examiner* — Khiem Nguyen
(74) *Attorney, Agent, or Firm* — Cheng-Ju Chiang (57) ABSTRACT

An exemplary atomizing device includes a main body, a mouthpiece, a liquid chamber, at least one heating element, and a permeating component. The main body defines an air inlet and an air passage. The air inlet is in communication with the air passage. The mouthpiece is arranged at an end of the main body. The mouthpiece defines an air outlet in communication with the air passage. The liquid chamber is configured for storing tobacco liquid. The at least one heating element is arranged in the air passage. The at least one heating element is configured for heating the tobacco liquid to form aerosol. The permeating component has a heat absorbing surface. The at least one heating element is in contact with the heat absorbing surface. The permeating component is configured for guiding the tobacco liquid to the heat absorbing surface for atomization.

17 Claims, 13 Drawing Sheets

ATOMIZING DEVICE AND ELECTRONIC CIGARETTE HAVING SAME

TECHNICAL FIELD

The present invention relates to electronic cigarettes, and particularly to an atomizing device and an electronic cigarette using same.

BACKGROUND ART

A typical electronic cigarette includes an atomizing device and a power supply. The atomizing device includes a liquid conducting component for absorbing tobacco liquid, and a heating wire for heating the tobacco liquid to from aerosol. The heating wire is wound around the liquid conducting component. However, a contact surface between the heating wire and the liquid conducting component is small. Accordingly, an amount of aerosol generated is limited, rendering unsatisfactory.

What are needed, therefore, are an atomizing device and an electronic cigarette using same, which can overcome the above shortcomings.

SUMMARY

An exemplary atomizing device includes a main body, a mouthpiece, a liquid chamber, at least one heating element, and a permeating component. The main body defines an air inlet and an air passage. The air inlet is in communication with the air passage. The mouthpiece is arranged at an end of the main body. The mouthpiece defines an air outlet in communication with the air passage. The liquid chamber is configured for storing tobacco liquid. The at least one heating element is arranged in the air passage. The at least one heating element is configured for heating the tobacco liquid to form aerosol. The permeating component has a heat absorbing surface. The at least one heating element is in contact with the heat absorbing surface. The permeating component is configured for guiding the tobacco liquid to the heat absorbing surface for atomization.

BRIEF DESCRIPTION OF THE DRAWINGS

Many aspects of the present disclosure can be better understood with reference to the following drawings. The components in the drawings are not necessarily drawn to scale, the emphasis instead being placed upon clearly illustrating the principles of the present disclosure. Moreover, in the drawings, like reference numerals designate corresponding parts throughout the several views.

DETAILED DESCRIPTION

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures and components have not been described in detail so as not to obscure the related relevant feature being described. Also, the description is not to be considered as limiting the scope of the embodiments described herein. The drawings are not necessarily to scale and the proportions of certain parts have been exaggerated to better illustrate details and features of the present disclosure.

The disclosure is illustrated by way of example and not by way of limitation in the figures of the accompanying drawings in which like references indicate similar elements. It should be noted that references to "an" or "one" embodiment in this disclosure are not necessarily to the same embodiment, and such references mean at least one.

Several definitions that apply throughout this disclosure will now be presented.

The term "outside" refers to a region that is beyond the outermost confines of a physical object. The term "inside" indicates that at least a portion of a region is partially contained within a boundary formed by the object. The term "substantially" is defined to be essentially conforming to the particular dimension, shape or other word that substantially modifies, such that the component need not be exact. For example, substantially cylindrical means that the object resembles a cylinder, but can have one or more deviations from a true cylinder. The term "comprising," when utilized, means "including, but not necessarily limited to"; it specifically indicates open-ended inclusion or membership in the so-described combination, group, series and the like.

Figure 1:
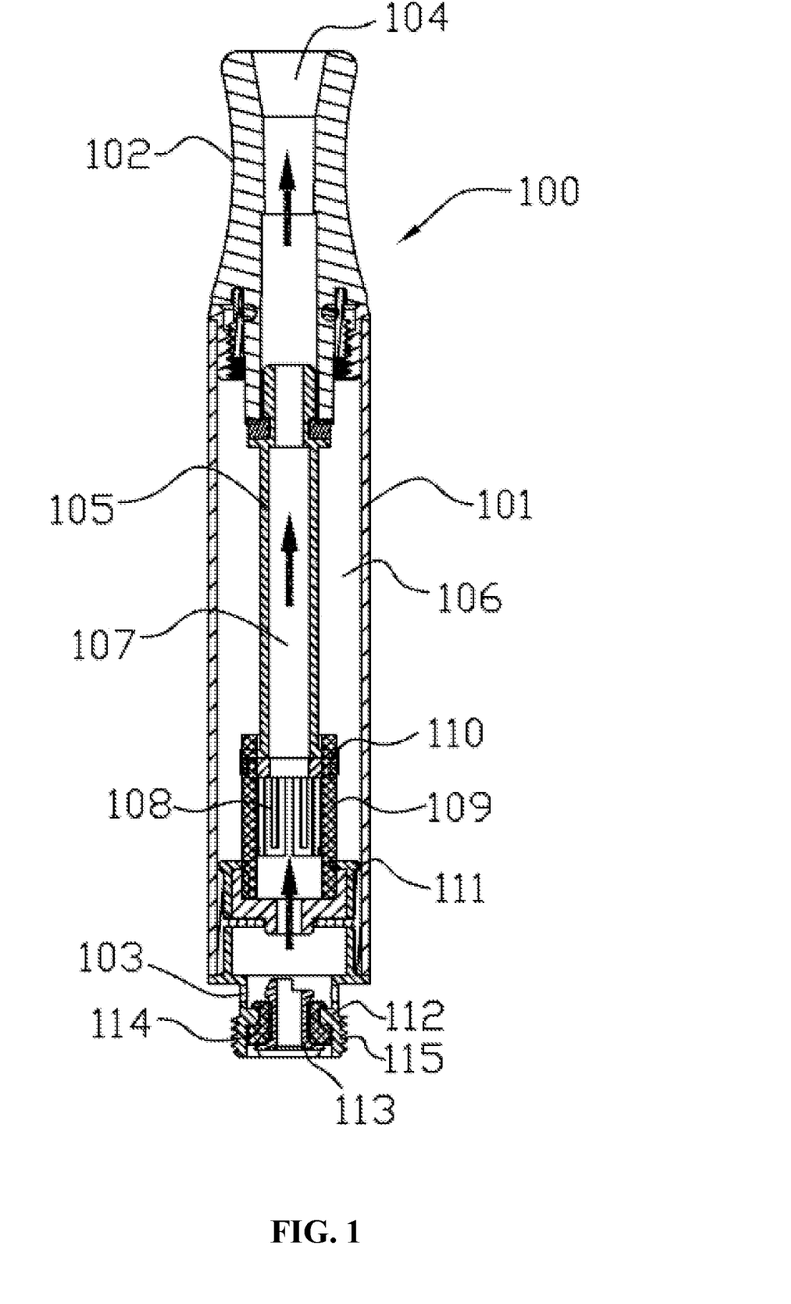
FIG. 1 is a cross-sectional view of an atomizing device according to a first embodiment.

Referring to FIG. 1, an atomizing device 100 includes a main body 101, a permeating component 109, and a liquid chamber 106. The liquid chamber 106 is configured (structured and arranged) for storing tobacco liquid. The main body 101 defines at least one air inlet 103. The atomizing device 100 further includes a mouthpiece 102 with an air outlet 104. An air passage 107 is formed between the air inlet 103 and the air outlet 104 in the main body 101. The mouthpiece 102 is detachably connected with the main body 101. When the mouthpiece 102 is coupled to the main body 101, the liquid chamber 106 is sealed. When the mouthpiece 102 is detached from the main body 101, tobacco liquid may be filled into the liquid chamber 106. At least one heating element 108 is arranged in the air passage 107. The heating element 108 is configured for heating the tobacco liquid to form aerosol. The permeating component 109 has a porous structure, and includes a heat absorbing surface. The heating element 108 is in contact with the heat absorbing surface. The tobacco liquid in the liquid chamber 106 permeates to the heat absorbing surface via capillary action, and then is heated by the heating element 108 to generate aerosol. The aerosol flows to the mouthpiece 102 via the air passage 107, and then is expelled from the air outlet 104 of the mouthpiece 102. The atomizing device 100 further includes a connection part at an end of the main body 101 away from the mouthpiece 102. The connection part includes a positive electrode connector 113 and a negative electrode connector 112. The positive connector 113 and the negative connector 112 are adapted for connecting to an external power supply. The positive connector 113 and the negative connector 112 are respectively electrically connected to two opposite ends of the heating element 108. An insulated ring 114 is sandwiched between the positive connector 113 and the negative connector 112. The negative connector 112 includes a threaded structure 115. When the atomizing device 100 is coupled to the power supply via the threaded structure 115, the heating element 108 is electrically connected with the power supply.

The permeating component 109 may be made of porous ceramic, glass fiber, or porous metallic material. At least one part of the permeating component 109 contacts with the tobacco liquid in the liquid chamber 106. Also referring to FIGS. 2-3, the permeating component 109 is hollow, and includes an inner surface 1091 and an outer surface 1092. The outer surface 1092 is in contact with the tobacco liquid, and the heating element 108 is formed on the inner surface 1091. The inner surface 1091 serves as the heat absorbing surface. The heating element 108 may be attached on the heat absorbing surface in the form of thin film, or be printed on the heat absorbing surface (described in detail later). In the present embodiment, the heat absorbing surface is large, so that a large amount of aerosol is formed in use.

Figure 2:
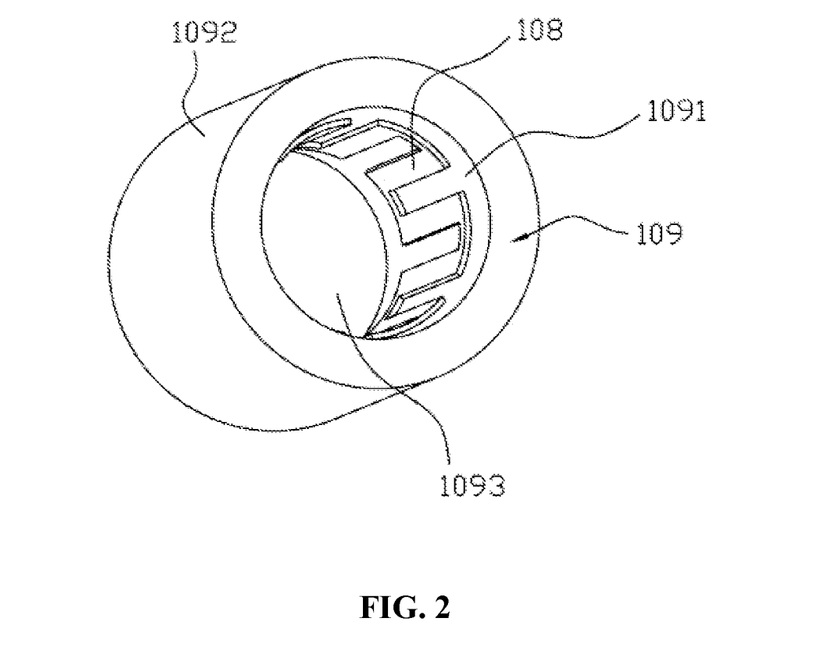
FIG. 2 is a perspective view of a permeating component and a heating element assembled with the permeating component in the atomizing device of FIG. 1.
Figure 3:
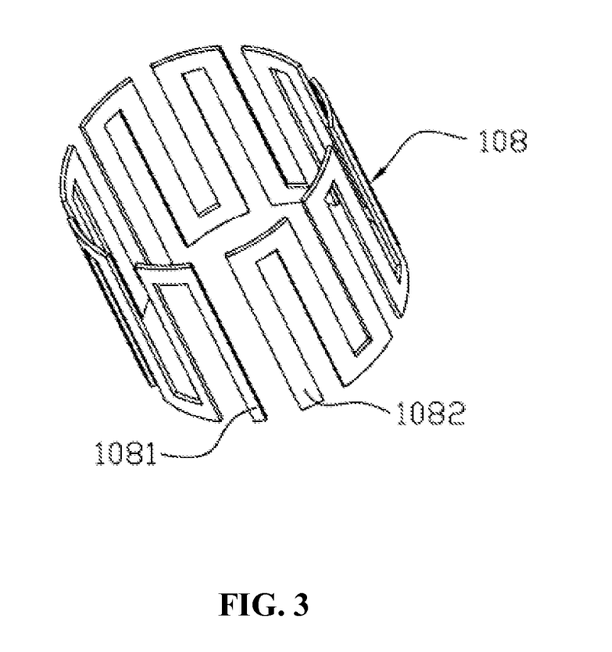
FIG. 3 is a perspective view of a heating element of FIG. 1.

The permeating component 109 is substantially annular, and defines a through hole 1093. The tobacco liquid permeates from the outer surface 1092 to the inner surface 1091 for atomization. It is to be understood that the permeating component 109 may be other shapes, for example, rectangular. In the present embodiment, the heating element 108 is a stripe in a snake shape. In detail, the heating element 108 is bent up and down repeatedly to form a shape of rectangular wave, and is then attached to the inner surface 1091. The heating element 108 is substantially annular as a whole. Two opposite ends 1081, 1082 are electrically connected to the positive electrode connector 113 and the negative electrode connector 112, respectively.

The atomizing device 100 further includes an air pipe 105 in the main body 101. The air pipe 105 and a hollow part of the permeating component 109 cooperatively form the air passage 107. The liquid chamber 106 surrounds the air passage 107. The air pipe 105 is substantially coaxially arranged in the main body 101. A top end of the air pipe 105 is hermetically coupled with the mouthpiece 102, and a bottom end of the air pipe 105 is connected to the permeating component 109. The air pipe 105, the permeating component 109, and the main body 101 cooperatively define an annular space as the liquid chamber 106. A top end of the permeating component 109 is coupled to the air pipe 105 via a top silica holder, and a bottom end of the permeating component 109 is coupled to the main body 101 with a bottom silica holder 111, avoiding liquid leakage.

Figure 4:
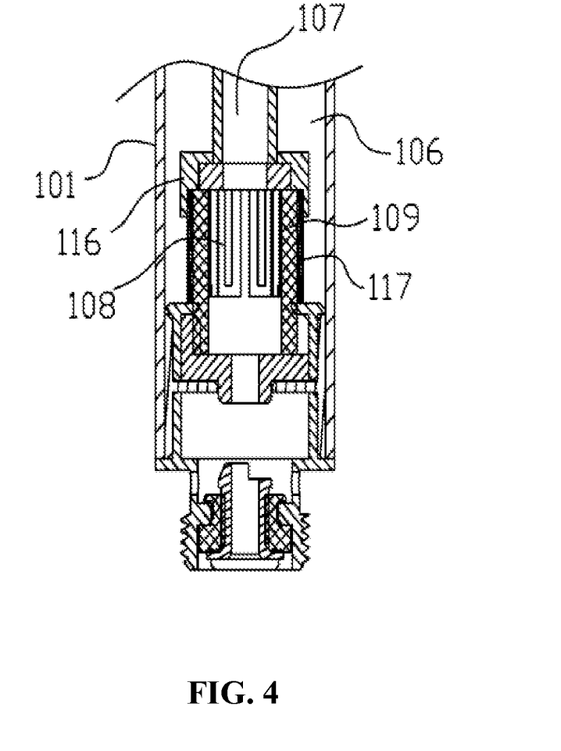
FIG. 4 is a cross-sectional view of an atomizing device with a liquid absorbing layer wrapping around the permeating component.

Referring to FIG. 4, quite usefully, a liquid absorbing layer 117 is provided on part of the permeating component 109, which is in contact with tobacco liquid. The liquid absorbing layer 117 is configured for absorbing tobacco liquid. The liquid absorbing layer 117 may be made of fiber cotton or sponge. The liquid absorbing layer 117 is wrapped around the annular permeating component, and is fixed by the fixing holder 116. The liquid absorbing layer 117 can hold tobacco liquid absorbed, and then the tobacco liquid in the liquid absorbing layer 117 gradually permeates the permeating component 109. Accordingly, it is prevented that the tobacco liquid directly permeates the permeating component 109 too quickly, which may lead to liquid leakage into the air passage 107.

Figure 5:
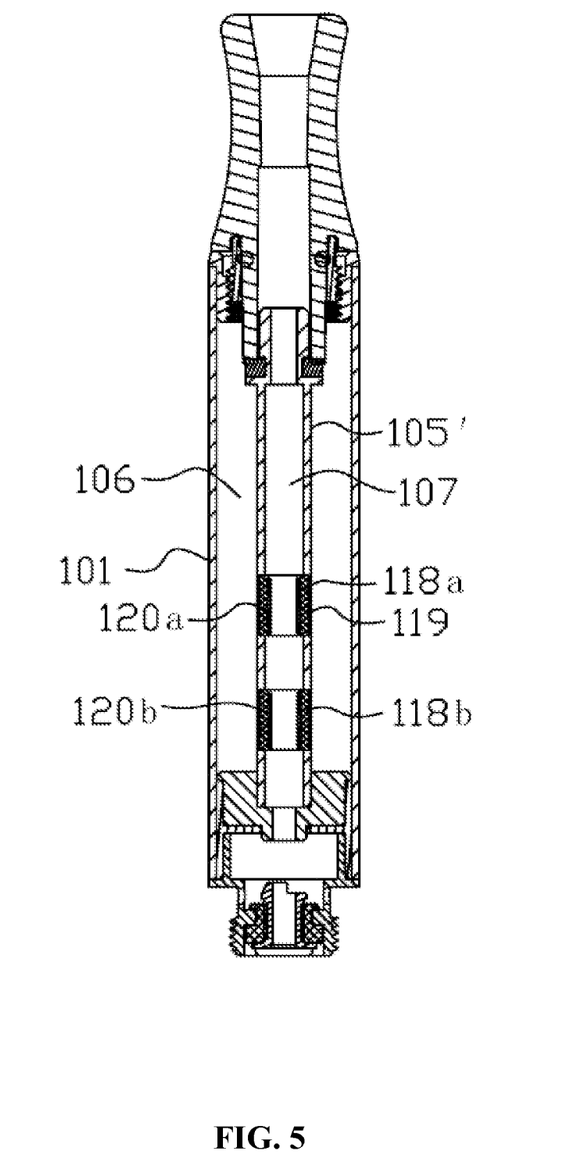
FIG. 5 is a cross-sectional view of an atomizing device according to a second embodiment.

Referring to FIG. 5, the atomizing device includes two heating elements. The air pipe 105' is oriented along a central axis of the main body 101. The air pipe 105' and the main body 101 cooperatively define the liquid chamber 106. The air pipe 105' defines an air passage 107. A first heating element 120a and a second heating element 120b are arranged in the air passage 107. The first heating element 120a and the second heating element 120b may be connected to a power supply in series or in parallel. The first heating element 120a and the second heating element 120b are arranged in a first permeating component 118a and a second permeating component 118b, respectively. The first permeating component 118a and the second permeating component 118b each have an identical structure as the permeating component 109 in FIG. 2. The air pipe 105' defines a plurality of openings 119 arranged along a central axis. The openings 119 are in communication with the liquid chamber 106. The first permeating component 118a and the second permeating component 118b are arranged spatially corresponding to the openings 119, so that the first permeating component 118a and the second permeating component 118b contacts with the tobacco liquid. The first heating element 120a and the second heating element 120b may be a heating film attached on an interior wall of the first permeating component 118a and the second permeating component 118b. Also, the first heating element 120a and the second heating element 120b may be a heating layer printed on the interior wall of the first permeating component 118a and the second permeating component 118b.

Figure 6:
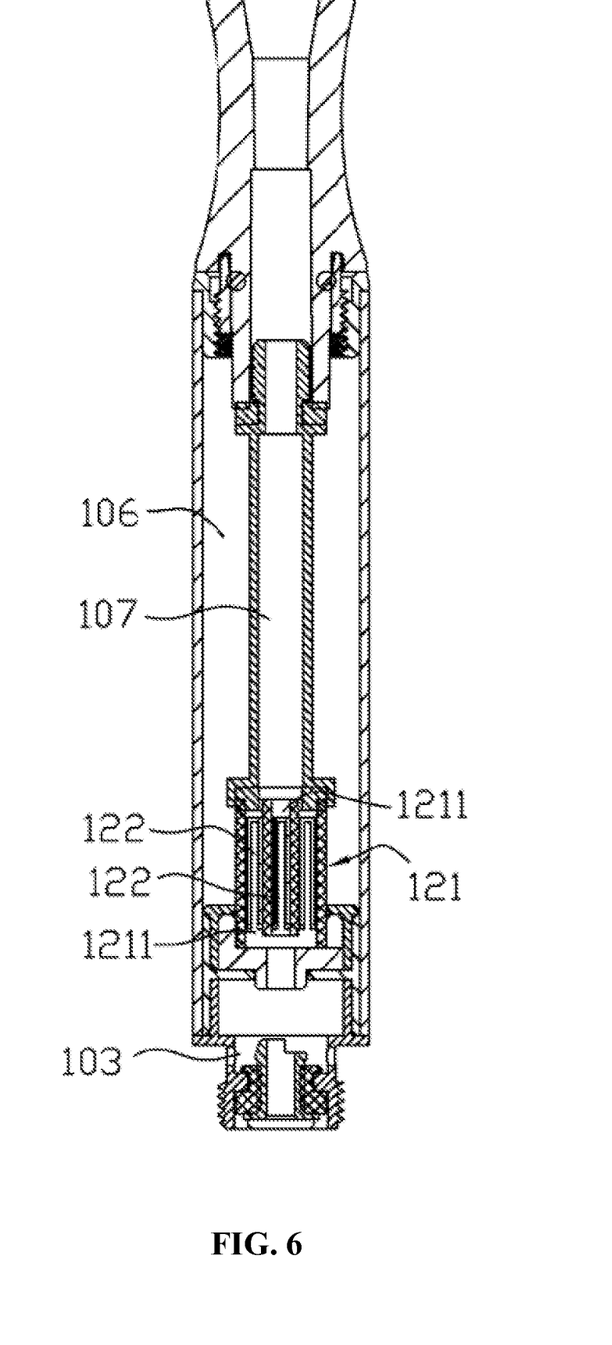
FIG. 6 is a cross-sectional view of an atomizing device according to a third embodiment, including a permeating component.
Figure 7:
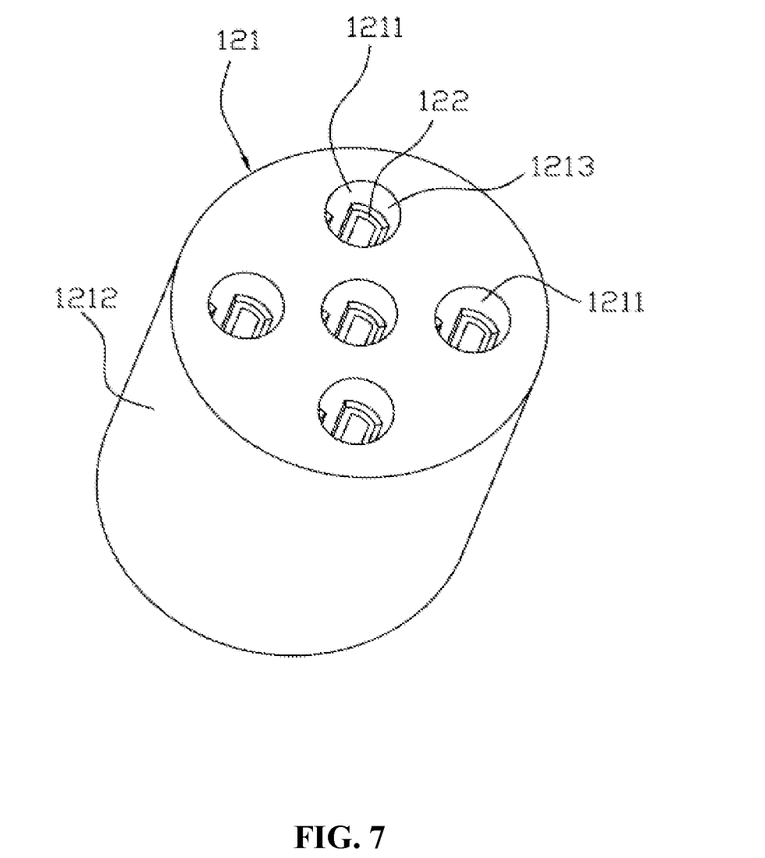
FIG. 7 is a perspective view of the permeating component of FIG. 6.

Referring to FIGS. 6-7, a variation of the atomizing device 100 of FIG. 1 is shown. The variation is similar to the atomizing device 100, except the structure of the permeating component. The permeating component 121 is substantially a cylinder and defines a plurality of air holes 1211 extending along a direction parallel to an axis. Each air hole 1211 includes an interior wall 1213 functioning as a heat absorbing surface. A heating element 122 is arranged on the interior wall 1213 of each air hole 1211. An external sidewall 1212 of the permeating component 121 is in contact with the tobacco liquid in the liquid chamber 106. The air holes 1211 are arranged in an array. The air holes 1211 are in communication with the air passage 107. The heating elements 122 are similar to that of FIG. 3.

Figure 8:
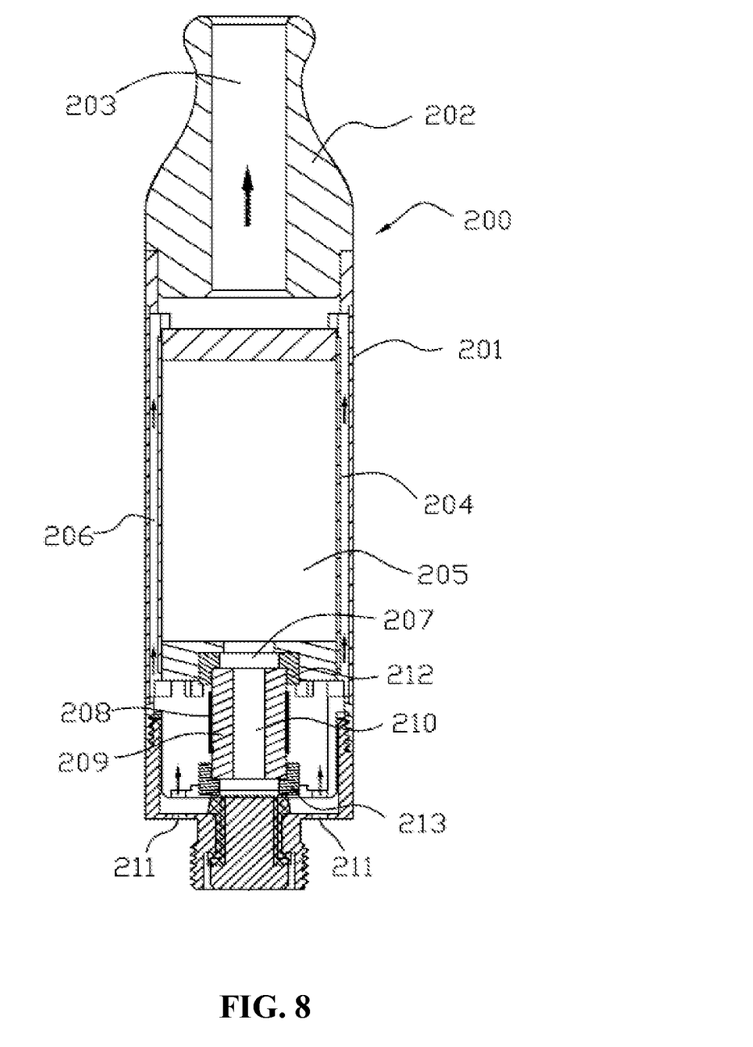
FIG. 8 is a cross-sectional view of an atomizing device according to a fourth embodiment, including a permeating component and a heating element.
Figure 9:
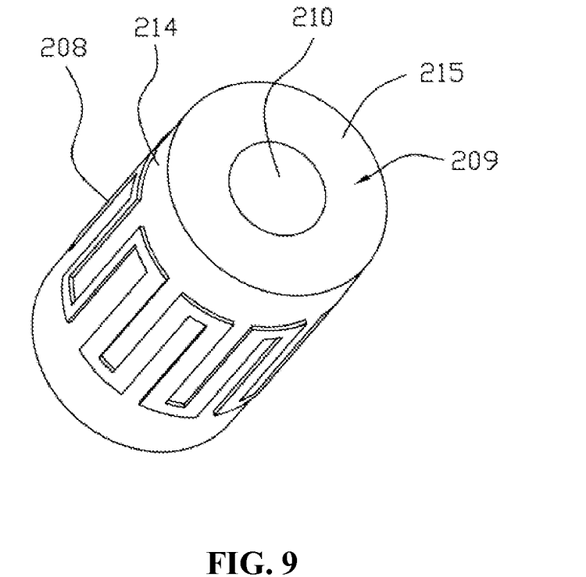
FIG. 9 is a perspective view of the permeating component assembled with the heating element of FIG. 8.

Referring to FIGS. 8-9, an atomizing device 200 according to a fourth embodiment is shown. The atomizing device 200 includes a main body 201. The main body 201 defines an air inlet 211 at one end. A mouthpiece 202 is provided at the other end of the main body 201. The mouthpiece 202 defines an air outlet 203. A liquid supply 204 is disposed in the main body 201, and includes a liquid chamber 205 for storing tobacco liquid. Air from the air inlet 211 goes along a gap 206 between the liquid supply 204 and the main body 201, and is then expelled via the air outlet 203. The gap 206 forms part of air passage. The liquid supply 204 includes a liquid outlet 207 at an end. The permeating component 209 is coupled to the liquid outlet 207. In detail, the permeating component 209 is hollow and annular. A top end of the permeating component 209 is inserted into the liquid outlet 207, and is hermetically connected with the liquid supply 204 via a fixing holder 212. A bottom end of the permeating component 209 is hermetically connected to a main body 201 via another fixing holder 213. The tobacco liquid in the liquid chamber 205 can flow into a through hole 210 of the permeating component 209. The tobacco liquid can permeate from an interior wall to an exterior wall 214. A heating element 208 is arranged on the exterior wall 214. The heating element 208 is a stripe in a snake shape. The exterior wall 214 serves as a heat absorbing surface. In addition, a top surface 215 of the permeating component 209 may be in contact with the tobacco liquid, so that some tobacco liquid permeates into the permeating component 209 via the top surface 215.

Figure 10:
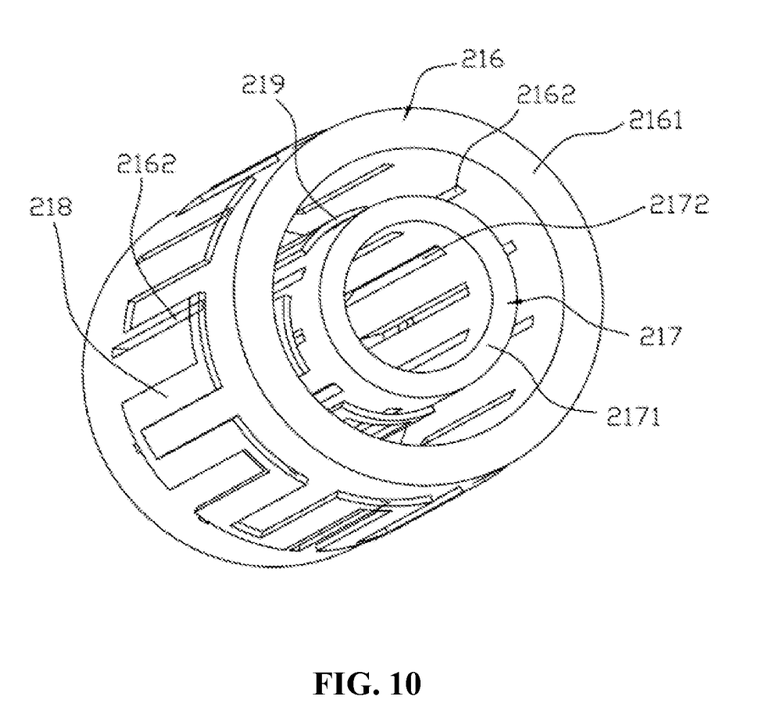
FIG. 10 is a perspective view of a permeating component according to a fifth embodiment.

Referring to FIG. 10, a permeating component according to the fifth embodiment is shown. The permeating component includes a plurality of porous bodies, and each permeating component is tube-shaped. The porous bodies are arranged in the form of one nesting another. In the present embodiment, the permeating component includes an inner porous body 217 and an outer porous body 216. The inner porous body 217 is nested in the outer porous body 216. A heating element 218 is attached on an outer surface of the porous body 216, and a heating element 219 is attached on an outer surface of the porous body 217. It is to be understood that in other embodiments, the heating element may be formed on an inner surface of the porous bodies 216, 217. It is to be understood that in other embodiments, the heating element may be formed on both of the outer surface and the inner surface of the porous bodies 216, 217. An end surface 2161 of the porous body 216 and an end surface 2171 of the porous body 217 are in contact with tobacco liquid. Accordingly, the tobacco liquid permeates the porous bodies 216, 217 via the end surfaces 2161, 2171, and is then conveyed to an outer surface (a heat absorbing surface) of the porous bodies 216, 217 for atomization. The porous body 217 includes a hollow portion communicating with air passage. The porous body 216 defines an air groove 2162 in a sidewall, while the porous body 217 defines an air groove 2172 in a sidewall. Aerosol generated by heat absorbing surfaces of the porous bodies 216, 217 goes through air grooves 2162, 2172, and then goes along air passage to mouthpiece.

Figure 11:
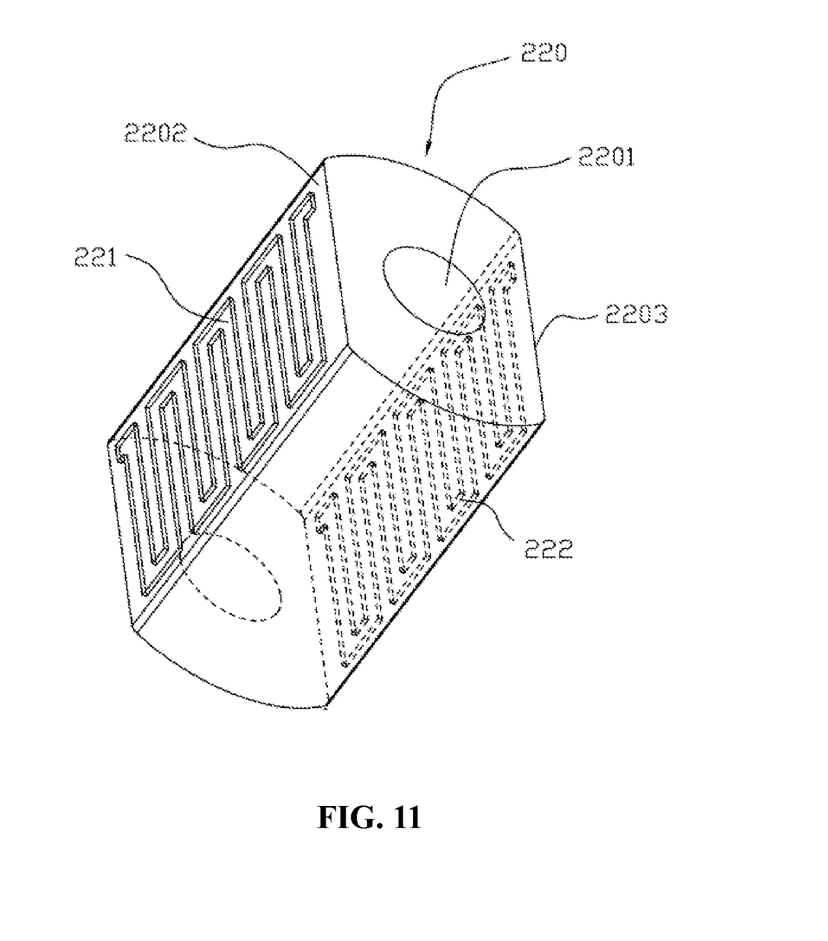
FIG. 11 is a perspective view of a variation of the permeating component in FIG. 8.

Referring to FIG. 11, as a variation of the permeating component 209 in FIG. 8, a permeating component 220 is shown. The permeating component 220 is substantially rectangular. The permeating component 220 is made of porous ceramic, fiber, or porous metal. The permeating component 220 defines a chamber 2201 in a central portion. When the permeating component 220 is assembled in an atomizing device, the chamber 2201 communicates with the liquid chamber 205, so that the tobacco liquid can enter the chamber 2201. The permeating component 220 includes two opposite planar surfaces, serving as heat absorbing surface 2202, 2203. A heating element 221 is arranged on the heat absorbing surface 2202, and a heating element 222 is arranged on the heat absorbing surface 2203. The heating elements 221, 222 each are stripes a snake shape.

Figure 12:
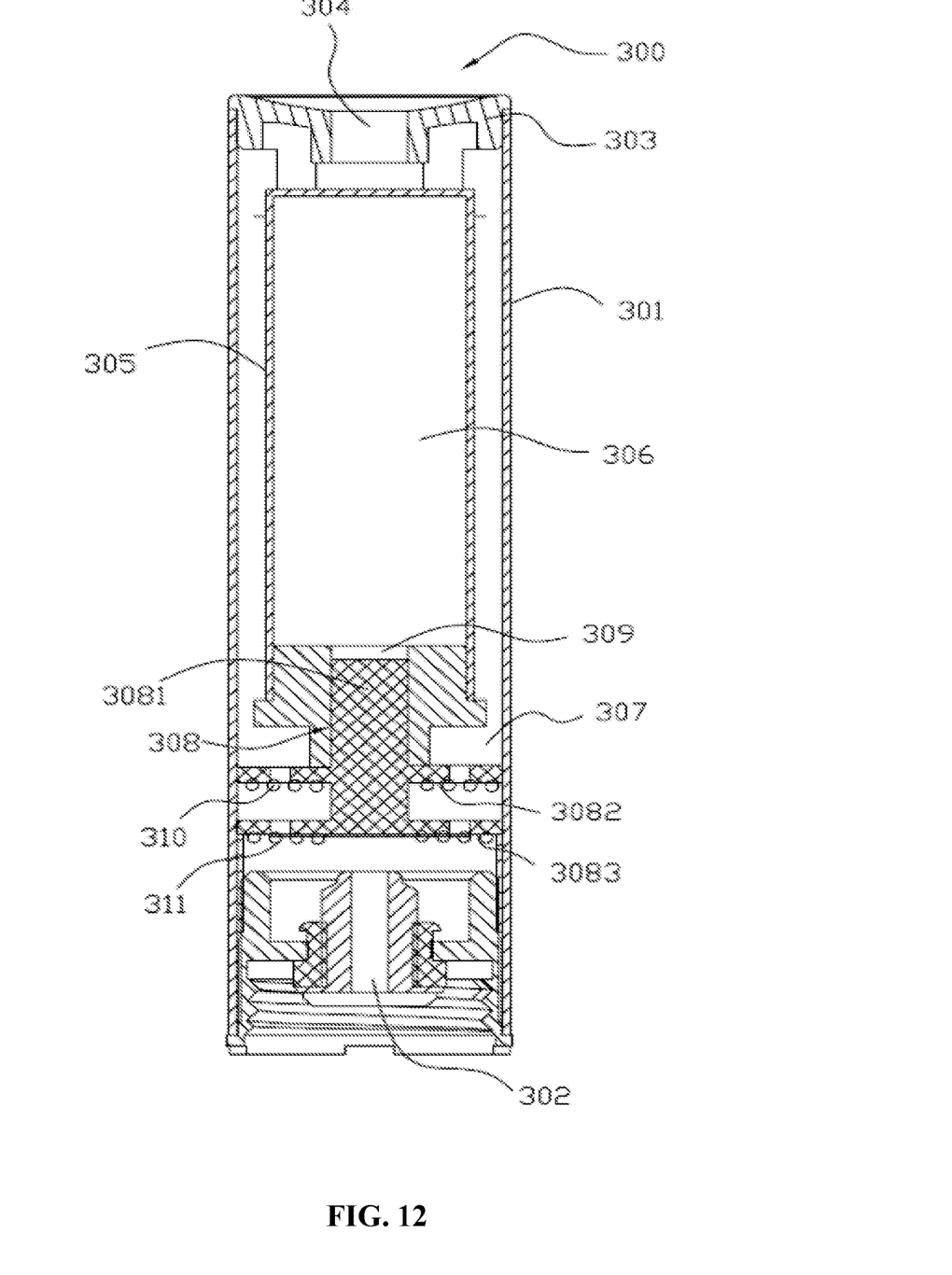
FIG. 12 is a cross-sectional view of an atomizing device according to a sixth embodiment.
Figure 13:
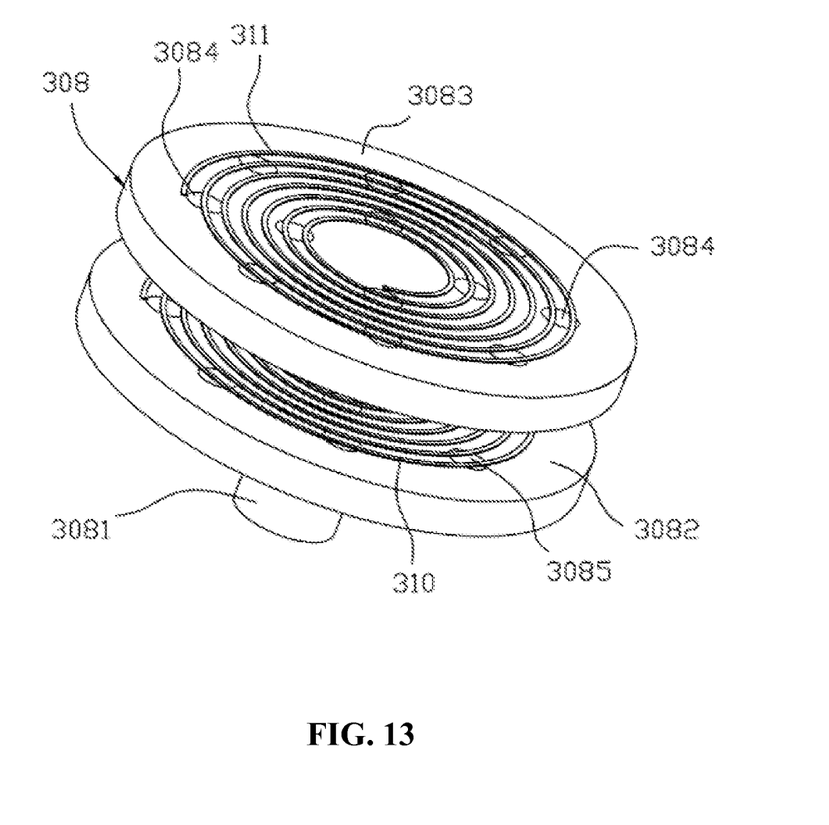
FIG. 13 is a perspective view of a permeating component assembled with heating elements of the atomizing device of FIG. 12.

Referring to FIGS. 12-13, an atomizing device 300 according to a sixth embodiment is shown. The atomizing device 300 includes a main body 301, and a liquid supply 305 received in the main body 301. The liquid supply 305 defines a liquid chamber 306 for storing tobacco liquid. The main body 301 defines an air inlet 302 at a first end. A mouthpiece 303 is provided at an opposite second end of the main body 301. The mouthpiece 303 defines an air outlet 304. An air passage 307 is oriented along an axial direction of the main body 301. The air passage 307 is in communication with the air inlet 302 and the air outlet 304. The liquid supply 305 defines a liquid outlet 309 at one end. The permeating component 308 includes an inserting part 3081 and two disks integrally formed. The inserting part 3081 and the two disks are made of an identical porous material. The inserting part 3081 is configured for inserting into the liquid outlet 309 to absorb tobacco liquid. The two disks include two heat absorbing surfaces 3082, 3083. The two heat absorbing surfaces 3082, 3083 are arranged along an axial direction of the air passage 307 in a parallel manner. A heating element 310 is arranged on the heat absorbing surface 3082, and a heating element 311 is attached on the heat absorbing surface 3083. The heating elements 310, 311 are heating wires wound in a spiral structure. The heat absorbing surface 3082 defines a plurality of air holes 3085, and the heat absorbing surface 3083 defines a plurality of air holes 3084. The tobacco liquid absorbed in the inserting part 3081 is conveyed to the heat absorbing surfaces 3082, 3083, and is then heated to form aerosol. The aerosol flows into the air passage 307 via air holes 3085, 3084.

Figure 14:
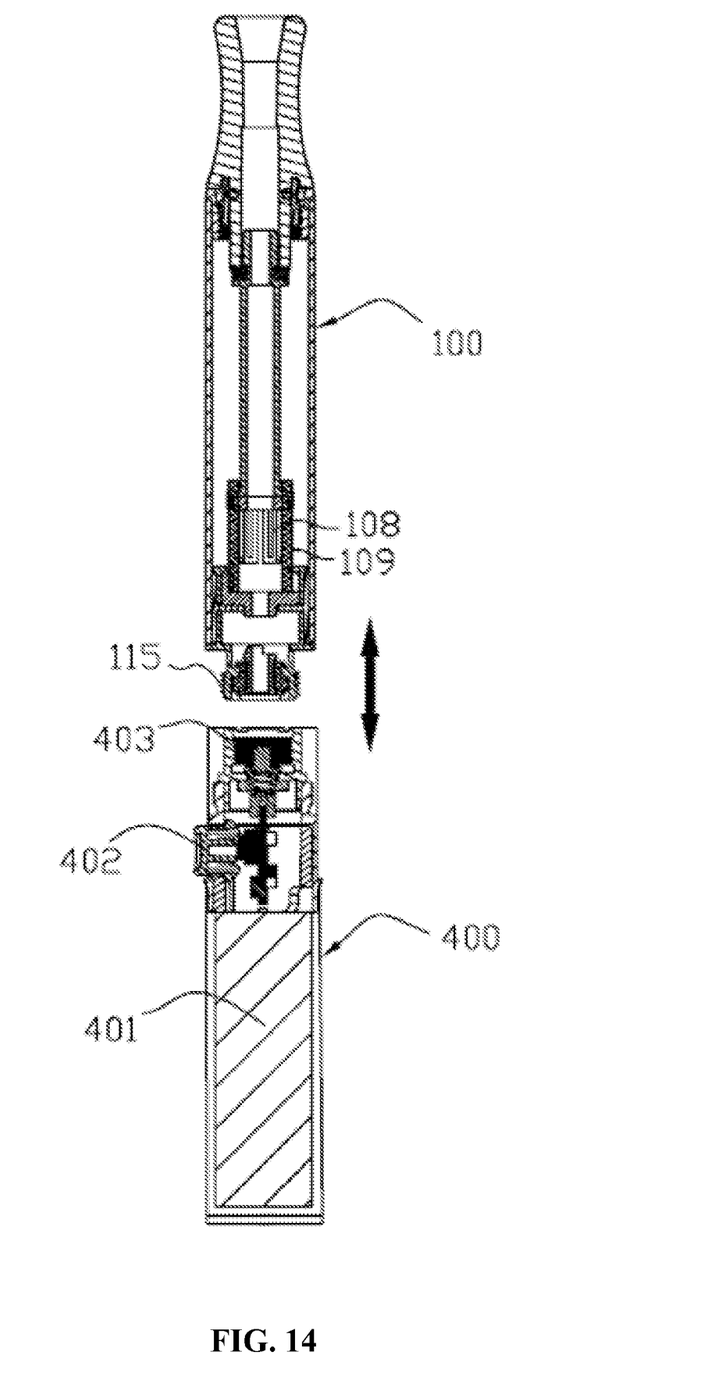
FIG. 14 is a cross-sectional view of an electronic cigarette according to a seventh embodiment.

Referring to FIG. 14, an electronic cigarette includes the atomizing device 100 and a power supply 400. The power supply includes a battery 401 and a button 402. The atomizing device 100 and a power supply 400 are detachably coupled. In the present embodiment, the atomizing device 100 includes an external screw structure 115 at an end, and the power supply 400 includes an internal screw structure 403 at one end. The atomizing device 100 and a power supply 400 are coupled via the external screw structure 115 and the internal screw structure 403. In use, when the button 402 is pressed, the heating element 108 is powered on, and aerosol is generated.

Figure 15:
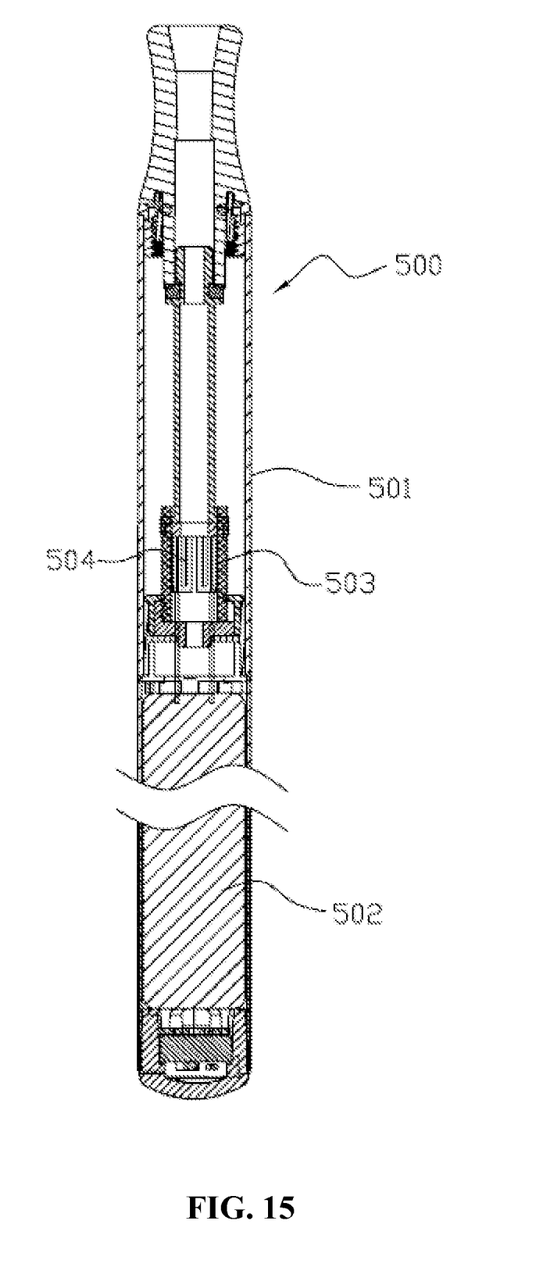
FIG. 15 is a cross-sectional view of an electronic cigarette according to an eighth embodiment.

Referring to FIG. 15, an electronic cigarette 500 is similar to the electronic cigarette 400 of FIG. 14, except that the electronic cigarette 500 has a one-piece structure. The electronic cigarette 500 includes a main body 501, a liquid chamber in the main body, a heating element 504, and a permeating component 503. The liquid chamber, the heating element 504, and the permeating component 503 are the same as corresponding components in FIG. 1. The main body 501 includes a power supply 502 inside. The heating element 504 is electrically connected to power supply 502.

It is understood that the above-described embodiments are intended to illustrate rather than limit the disclosure. Variations may be made to the embodiments and methods without departing from the spirit of the disclosure. Accordingly, it is appropriate that the appended claims be construed broadly and in a manner consistent with the scope of the disclosure.

What is claimed is:

1. An atomizing device, comprising:
   a main body defining an air inlet and an air passage, the air inlet being in communication with the air passage;
   a mouthpiece arranged at an end of the main body, the mouthpiece defining an air outlet, the air outlet being in communication with the air passage;

a liquid chamber in the main body, the liquid chamber being configured for storing tobacco liquid;

at least one heating element arranged in the air passage, the at least one heating element being configured for heating the tobacco liquid to form aerosol; and a permeating component having a heat absorbing surface, the at least one heating element being in contact with the heat absorbing surface, the permeating component being configured for guiding the tobacco liquid to the heat absorbing surface for atomization.

2. The atomizing device according to claim 1, wherein at least one part of the permeating component is in contact with the tobacco liquid in the liquid chamber.

3. The atomizing device according to claim 2, further comprising a liquid absorbing layer on part of the permeating component in contact with the tobacco liquid, wherein the liquid absorbing layer is configured for absorbing the tobacco liquid.

4. The atomizing device according to claim 3, wherein the liquid absorbing layer is made of fiber cotton or sponge.

5. The atomizing device according to claim 1, wherein the at least one heating element is stripe-shaped, and is attached to the heat absorbing surface, or the at least one heating element comprises a heating layer printed on the heat absorbing surface.

6. The atomizing device according to claim 5, wherein the permeating component is substantially annular, the permeating component includes an interior wall and an exterior wall, the exterior wall contacts with the tobacco liquid, and the interior wall serves as the heat absorbing surface.

7. The atomizing device according to claim 6, further comprising an air pipe in the main body, wherein the air pipe and the permeating component cooperatively define an air passage, and the liquid chamber surrounds the air passage.

8. The atomizing device according to claim 5, wherein the permeating component is substantially cylindrical, and defines a plurality of air holes oriented along a direction parallel to an axial direction thereof, each air hole comprises an interior wall functioning as the heat absorbing surface.

9. The atomizing device according to claim 5, wherein the permeating component is substantially annular, the permeating component comprises an interior wall and an exterior wall, the exterior wall serves as the heat absorbing surface, the at least one heating element is attached to the exterior wall, and the interior wall is in contact with the tobacco liquid.

10. The atomizing device according to claim 5, wherein the permeating component comprises a plurality of tube-shaped porous bodies, the porous bodies are arranged in the form of one nesting another, the at least one heating element comprises a plurality of heating elements, and each heating element is arranged on an inner surface/an outer surface of a correspondent permeating component.

11. The atomizing device according to claim 5, wherein the at least one heating element comprises a plurality of heating elements arranged along the air passage.

12. The atomizing device according to claim 6, wherein the at least one heating element is a stripe in a snake shape.

13. The atomizing device according to claim 1, wherein the at least one heating element comprises a plurality of heating wires, and each heating wire is wound in a spiral form.

14. The atomizing device according to claim 13, wherein the permeating component comprises a plurality of heat absorbing surfaces, the heat absorbing surfaces are arranged along an axial direction of the air passage in a parallel manner, and each heating element is arranged on a corresponding heat absorbing surface.

15. An electronic cigarette, comprising:
an atomizing device according to claim 1; and
a power supply configured for supplying the atomizing device power.

16. The electronic cigarette according to claim 15, wherein the electronic cigarette is a one-piece electronic cigarette.

17. The electronic cigarette according to claim 15, wherein the atomizing device is detachably coupled with the power supply.

* * * * *